United States Patent

Arima et al.

[11] Patent Number: 5,623,100
[45] Date of Patent: Apr. 22, 1997

[54] ULTRASONIC INSPECTION AND IMAGING INTSTRUMENT

[75] Inventors: Yukio Arima, Thukuba; Toshihiro Kimura, Ibaraki-ken; Yuichi Kunitomo, Tsuchiura; Tadatoshi Shimamura, Ishioka; Takeshi Nishiduka, Ibaraki-ken; Ken Takeuchi, Tsuchiura, all of Japan

[73] Assignee: Hitachi Construction Machinery Co., Ltd., Tokyo, Japan

[21] Appl. No.: 505,535

[22] Filed: Jul. 21, 1995

[51] Int. Cl.⁶ ............................. G01N 29/06
[52] U.S. Cl. ............................. 73/611; 73/613
[58] Field of Search ............... 73/610, 611, 612, 73/614, 615, 616, 613, 602, 597, 598, 600, 599

[56] References Cited

U.S. PATENT DOCUMENTS

| | | | |
|---|---|---|---|
| 3,744,301 | 7/1973 | Arave | 73/610 |
| 3,780,572 | 12/1973 | Rocha | 73/614 |
| 4,106,346 | 8/1978 | Matzuk | 73/614 |
| 4,137,776 | 2/1979 | Rudis et al. | 73/615 |
| 4,676,105 | 6/1987 | Matzuk | 73/602 |
| 4,700,711 | 10/1987 | Carlson | 73/612 |

*Primary Examiner*—Hezron E. Williams
*Assistant Examiner*—Nashmiya Ashraf
*Attorney, Agent, or Firm*—Fay, Sharpe, Beall, Fagan, Minnich & McKee

[57] ABSTRACT

In an ultrasonic inspection and imaging instrument, a pulse generator and a burst wave generator are provided in association with the activation of an ultrasonic probe by the pulse generator and in response to a measurement value obtained from a signal reception circuit portion. A first gate position is obtained with regard to an inspection portion in a sample, and then a second gate position for a burst wave measurement is set by correcting the first gate position. The burst wave measurement is performed by activating the burst wave generator.

9 Claims, 5 Drawing Sheets

ECHO WAVEFORM AT POSITION B

FIG.4(a)

ECHO WAVEFORM AT POSITION C

ULTRASONIC INSPECTION AND IMAGING INTSTRUMENT

BACKGROUND OF THE INVENTION

1. Field of the Invention

The present invention relates to an ultrasonic inspection and imaging instrument and, more particularly, relates to an ultrasonic inspection and imaging instrument using burst waves which permits ultrasonic measurement and imaging at high resolution with a simple operation without using high frequency signals, which have been necessary for high-resolution ultrasonic measurement and imaging.

2. Description of Related Art

An ultrasonic inspection and imaging instrument is capable of displaying the interior of an object to be inspected (a sample) in the form of a B- and a C-scope image. In order to obtain a clear image, an imaging instrument of this sort requires inputting of various measurement conditions including specifications of an ultrasonic probe (hereinafter Probe) such as the focal distance, the wave velocities at the current temperatures in the interior of a medium and the sample and the like, and in response thereto setting of the focus of the probe in the sample at a desired depth, a gate position, a gate width and the like.

When inspecting ICs with an ultrasonic inspection and imaging instrument, it is required to obtain an image with a high resolution at an interface in a thin sample such as a junction face between a semiconductor chip and a lead frame. For this reason it is required to use a probe having a high oscillation frequency and a narrow frequency band as well as to use an ultrasonic flaw detector having an excellent amplification characteristic at a high frequency. In addition thereto, it is further required to properly focus the probe and to set the gate position and the gate width which is still further required to be set as narrow as possible.

An ultrasonic inspection and imaging instrument of high resolution generally becomes expensive and requires skill for the measurement operation as the resolution thereof increases. Unlike the above, there are ultrasonic inspection and imaging instruments which permit to increase the resolution without using a high frequency. One of such ultrasonic inspection and imaging instruments makes use of an interference wave caused by an echo S from the surface of a sample and an interface echo F from an interface in the same, and another makes use of an interference wave caused by a lens echo and a sample echo. In these ultrasonic inspection and imaging instruments the ultrasonic wave used for the measurement is a burst wave (continuous wave) other than a pulse wave.

Figure 6A:
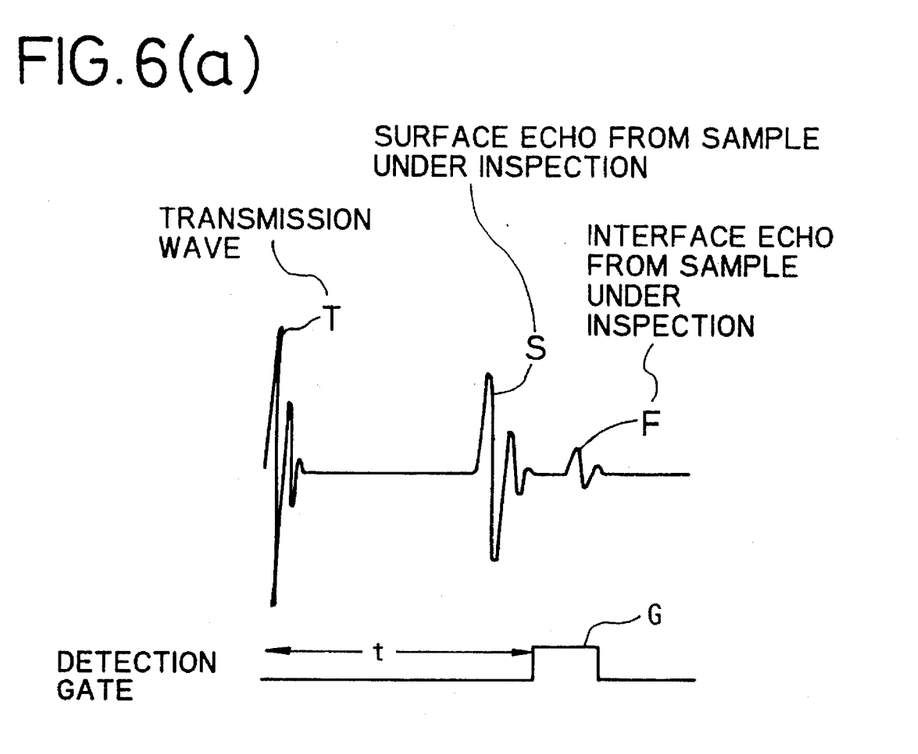
FIG. 6(a) is an explanatory view showing a relationship between gate position and gate width during pulse wave measurement.
Figure 6B:
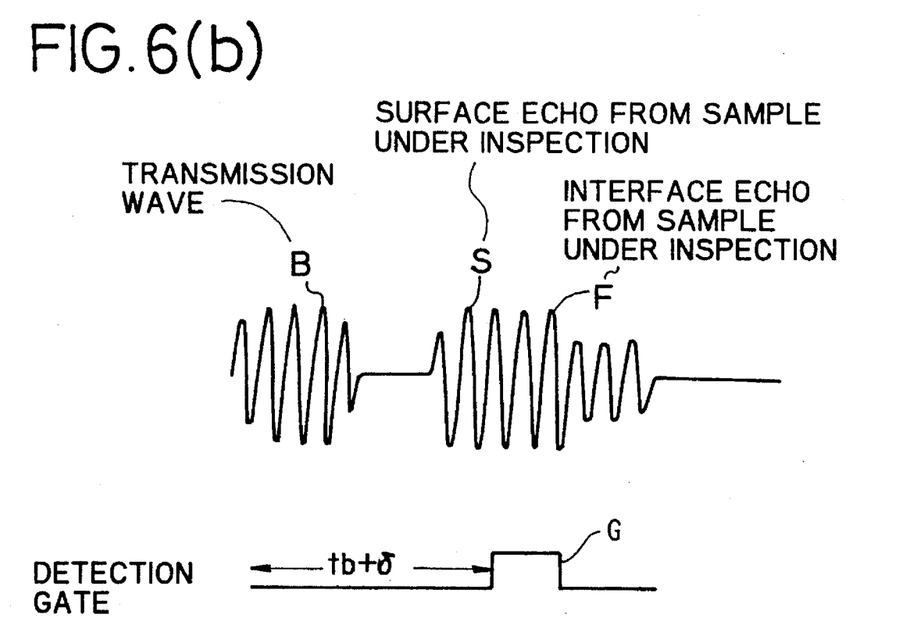
FIG. 6(b) is an explanatory view showing a relationship between gate position and gate width during burst wave measurement.

The ultrasonic inspection and imaging instruments making use of the burst wave are comparatively inexpensive because of the non-use of the high frequency- However, when observing a reflection wave (an A scope image) from a sample by making use of an oscilloscope and the like, an echo from the surface of the sample and an echo from the interface in the sample are observed as if a series of a continuous wave as shown in FIG. 6(b) which will be explained later therefore the focusing of the probe and the setting of the gate position are very difficult such that nonexperienced persons cannot handle instruments of this type.

Unlike the case of using pulse waves in which an operator discerns and determines the interface echo from the sample, the operator has to set a gate for sampling out a proper measurement image by selecting, through repeated trial and error, a gate position for obtaining an image having the most desirable resolution (a resolution representing a well-formed image in view of the image itself is called imaging resolution) while gradually shifting the gate position for a series of burst waves.

The above is also true with regard to the gate width. In a burst wave measurement wherein a gate having a broad width to the extent covering all interference waves is set, the gate width is normally insignificant. However, in order to increase the imaging resolution, in other words, in order to eliminate influences from portions other than noted portions, it is necessary to note a specific portion among the entirety of the interference waves and to extract the portion through the gate. In such case, it is necessary to set a gate having a comparatively narrow width at a proper position. In order to determine a proper gate width in such instance it is necessary to perform setting operations many times with various gate widths.

Further, with regard to the distance between the probe and the sample, a position which shows the most desirable resolution also has to be determined through trial and error while gradually varying the distance. In addition, it is further required to adjust the frequency of the burst wave in order to obtain a proper image.

In order to avoid the repetition of these operations as much as possible, with an ultrasonic inspection instrument using a pulse wave generator suitable for obtaining an image of a low resolution, an image at the interface in a sample is obtained beforehand and the gate position, gate width and distance between the probe and the sample at this instance are recorded. Thereafter the previously recorded gate position, gate width and distance between the probe and the sample are set for another ultrasonic inspection instrument using a burst wave generator.

However, with the above measurement it is necessary to use two sets of measurement instruments, and the gate position, gate width and distance between the probe and the sample which are obtained through the measurement instrument using a pulse wave generator suitable for obtaining an image of a low resolution are not necessarily proper ones for the measurement instrument using a burst wave generator. The probes themselves are different; in particular, the frequencies of the pulse wave and the burst wave used for the respective probes are different. Further, their signal transmission passages during signal transmission and reception are different. Still further, their beam routes according to the focusing positions are different.

These causes, in particular, affect the gate position. A relatively proper gate width can be determined when successively selecting gates from one having a broad width to one having a narrow width. Further, a relatively proper position for the probe is also determined when successively moving the probe toward an object or alternatively moving the probe away from the object. However, the above operations are based on a condition that the gate position is properly set. The gate position varies depending upon such as an object to be inspected and a flaw position, and has to be determined every time the object to be inspected is changed.

As a result, even when the two sets of measurement instruments are used, it takes time for adjusting operations for the measurement instrument using a burst wave generator and the measurement operations therewith are complex.

SUMMARY OF THE INVENTION

In order to reduce such complex operations it is contemplated to assemble these two measurement instruments into one unit and to perform a coarse measurement with pulse waves and thereafter to switch to a measurement with burst waves. However, even with such a unit it is necessary to exchange the probe for the pulse wave measurement for the probe for the burst wave measurement; therefore the facts are unchanged that the focusing positions, the signal transmission and reception passages, and the beam routes are different. Still further, the waveforms themselves of the pulse waves and the burst waves are different and their detection principles are also different; therefore it is difficult to eliminate the above explained adjusting operations.

An object of the present invention is to provide an ultrasonic inspection and imaging instrument using burst waves which permits to perform a measurement of a high resolution simply with an easy setting of a gate position and without using high frequency signals, which have been necessitated for high resolution ultrasonic measurement and imaging.

Another object of the present invention is to provide an ultrasonic inspection and imaging instrument using burst waves which permits to obtain an ultrasonic measurement image of a high resolution with simple operations.

The ultrasonic inspection and imaging instrument according to the present invention which achieves the above objects comprises a pulse generator; a burst signal generator which generates burst signals; a focusing type probe which contains the frequency of output pulses of the pulse generator and the frequency of the burst signals within the oscillation band thereof; a signal reception circuit portion which receives reception signals from the probe; a gate position setting means which activates the probe through the output pulses produced by activating the pulse generator to obtain a first gate position with regard to an inspection portion dependent upon a measurement value obtained from the signal reception circuit portion, corrects the first gate position to obtain a second gate position for burst wave measurement and sets the gate at the second gate position; and an ultrasonic measurement means which activates the probe by the burst signals with the gate at the second gate position having a predetermined gate width and performs an ultrasonic measurement on the inspection portion.

For example, during the pulse wave measurement when the same focusing type probe for the burst wave measurement (probe for burst waves) is used and the probe for the burst wave measurement is activated by pulse signals with reference to slice pulses of the burst signals, a difference in signal transmission conditions including the signal transmission passage of activating signals from the generation point thereof to the probe substantially disappears in the cases of the pulse wave measurement and of the burst wave measurement. Accordingly, the error between the first peak of the burst wave signals and the first peak of the pulse wave signals in defect echo reception signals corresponds to a deviation quantity of the generating positions of the defect echoes. When setting the gate position for the burst wave measurement by taking into account the deviation quantity, a proper gate width selected during the pulse wave measurement in view of the burst wave measurement and the height of the probe (measurement position) during the pulse wave measurement can be used as they are without significant errors. Further, if the above deviation quantity is corrected and the slice pulses of the burst waves are used as a reference, the deviation of the defect echo generating positions can be confined in a range of the peak deviation error corresponding to about a half cycle of the burst wave.

The quantity to be corrected at this instance is in a range of deviation quantity caused by the difference of the measurement methods when switched from the pulse wave measurement to the burst wave measurement. Accordingly, when the gate position setting means is designed to be provided with a manually operable gate position adjusting circuit to correct the deviation quantity, a proper gate position for the burst wave measurement is obtained with the manually operable gate position adjusting circuit.

In this instance, the gate position obtained during the pulse wave measurement with the same probe is used as a reference; therefore the adjusting range (i.e. the above correction range) during the burst wave measurement is limited so that the adjusting range of the above gate position adjusting circuit can be narrowed and the adjustment thereof is facilitated. Further, for example even with a burst wave measurement with no adjustment, a mostly optimum measurement picture image or one close thereto can be obtained.

When activating the probe with pulse signals with reference to the slice pulses of the burst waves and performing a measurement for a high imaging resolution with a narrow gate width, a deviation quantity ($\Delta t$) between the generation timing of a burst signal and the generation timing of an activating pulse signal plays a significant role. Accordingly, the deviation quantity ($\Delta t$) is measured beforehand and the gate position obtained during the pulse wave measurement is corrected by the timing deviation quantity ($\Delta t$). Thereby, a burst wave measurement for a high imaging resolution with a narrow gate width is realized.

Alternatively, instead of using the slice pulses of the burst waves, when the slice pulses are generated with reference to synchronous pulses or signal transmission pulses in the side of the pulse wave measurement and thereafter the burst waves are sliced out from the original continuous signals with the thus generated slice pulses, the first peak position of the burst wave signals generated by the sliced burst signals constitutes a deviation error by a time range corresponding to one cycle of the continuous wave before slicing out the burst signals, because the synchronous pulses or the signal transmission pulses in the side of the pulse wave measurement and the continuous signals before slicing out the burst signals are not in synchronism with respect to their phases; therefore, the deviation quantity between the first peak positions of the pulse wave signals and of the burst wave signals in the defect echo reception signals cannot be limited within the above mentioned range corresponding to a half cycle of the burst wave. Thereby, the deviation quantity to be corrected increases accordingly, and when it is required to perform a measurement of a further high imaging resolution, it is preferable to use the slice pulses from the burst waves as the reference.

DESCRIPTION OF THE PREFERRED EMBODIMENT

Figure 1:
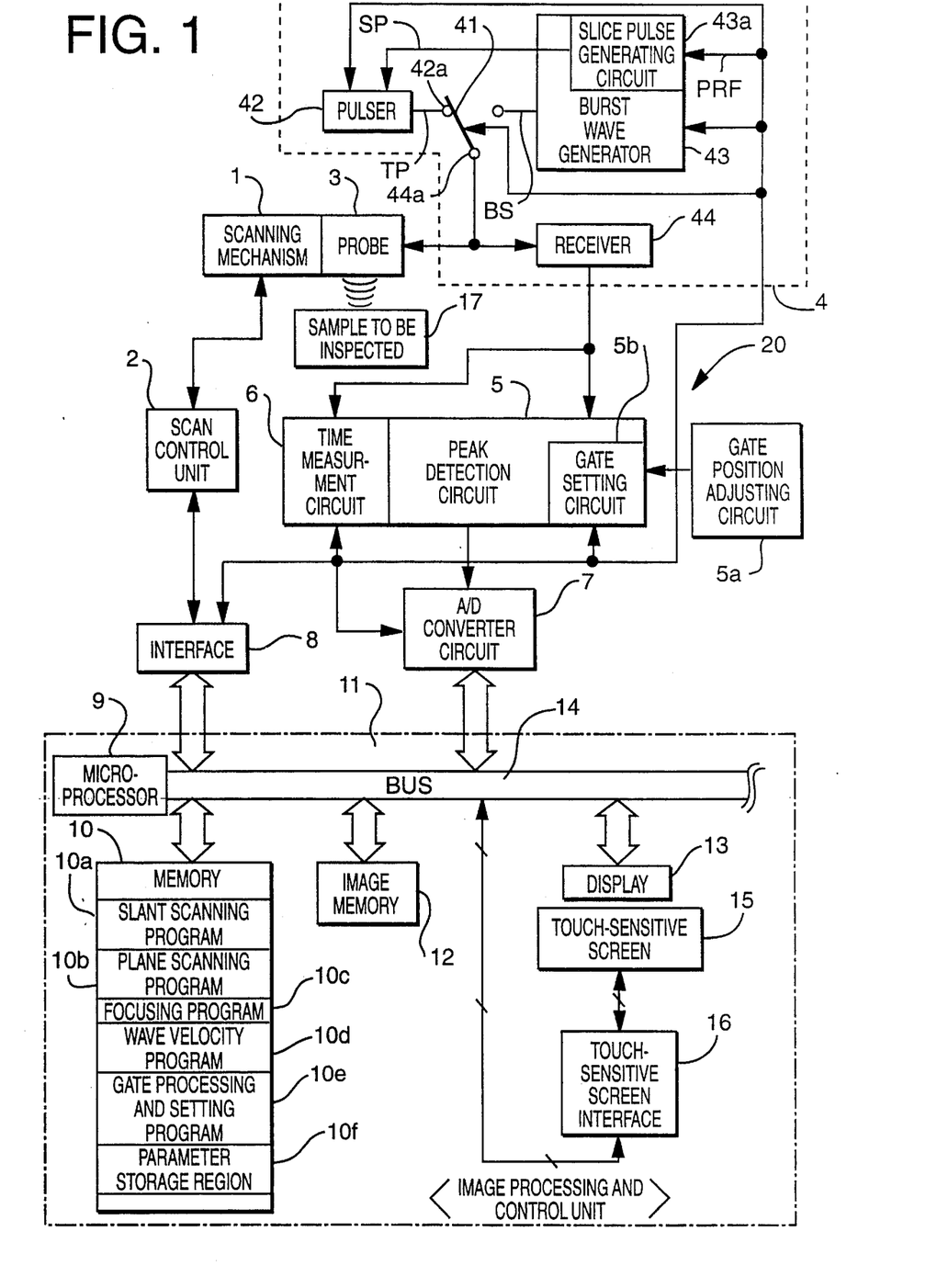
FIG. 1 is a block diagram of an embodiment of an ultrasonic inspection and imaging instrument according to the present invention.

FIG. 1 shows an ultrasonic inspection and imaging instrument 20 and a scanning mechanism 1 having an XYZ moving mechanism. A focusing type probe 3 is fitted to the scanning mechanism 1 and used for the main scanning of a sample (an object to be inspected) 17 in the X-direction and for the subscanning of the sample in the Y-direction.

The ultrasonic inspection and imaging instrument 20 obtains measured values from which an A-scope image at each measurement point is obtained by the XY scanning, based on which it produces display data on a B-scope image and display data on a C-scope image and displays the B- and the C-scope image.

Figure 3:
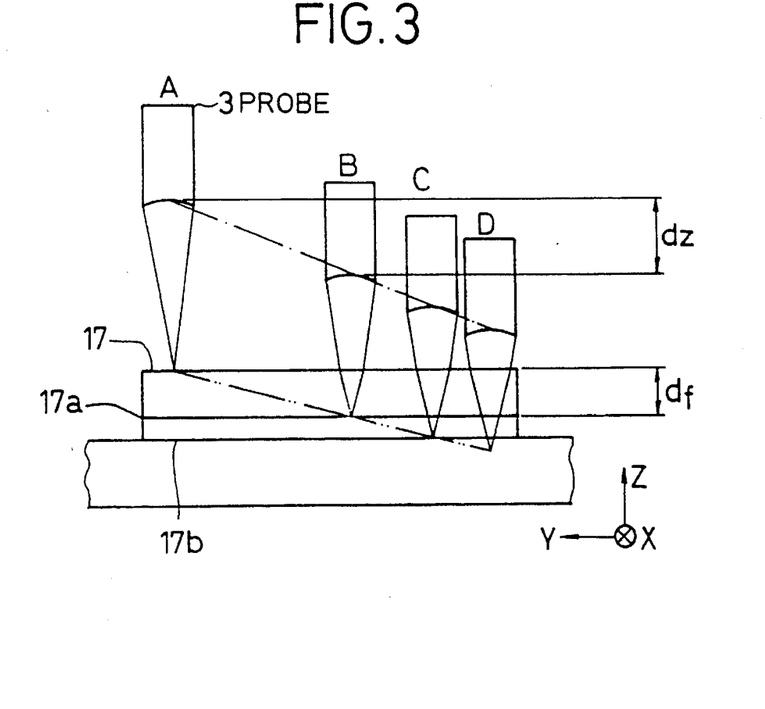
FIG. 3 is an explanatory view of the focusing process.

The sample 17 in the present embodiment is an electronic part such as an IC, and an interface, such as a face of a lead frame and a junction face between an IC chip and a ceramic substrate (or a base) on which the IC chip is adhered which constitutes a specific object face to be inspected, exists at a certain depth df from the surface of the sample 17 (see FIG. 3).

The scanning mechanism 1 is controlled by a scanning control unit 2, which is in turn controlled by an image processing and controlling unit (hereinafter called control unit) 11 via an interface 8. The probe 3 is connected to an ultrasonic flaw detector 4 comprising a change-over circuit 41, a pulser 42, a burst wave generator 43 and a reception signal amplifying circuit 44.

The reception signal amplifying circuit 44 receives either the output from the pulser 42 or the output from the burst wave generator 43 through the change-over operation by the change-over circuit 41. The change-over signal is formed by a control signal from the control unit 11 which is explained later. Further, synchronous pulses SP (see FIG. 5(a)) for the pulser 42 are generated from a slice pulse generating circuit 43a which is provided in the burst wave generator 43 and generates slice pulses PRFS (see FIG. 5(a)) which slice out burst signals from continuous signals. In response to the synchronous pulses SP the pulser 42 sends out signal transmission pulses TP (see FIG. 5(a)) to the probe 3.

The control unit 11 generates a control signal for repetition pulses PRF which depend on the measurement period and applies the same to the slice pulse generating circuit 43a in the burst wave generator. Further, when performing the pulse wave measurement in which the probe 3 is activated by pulse signals to generate pulse waves, an enable signal which causes to operate the slice pulse generating circuit 43a and the pulser 42 is applied to the both. When performing burst wave measurement in which the probe 3 is activated by burst signals BS (see FIG. 5(a)) to generate burst waves an enable signal is sent out which causes to operate the burst wave generator 43. Further, the slice pulse generating circuit 43a generates the slice pulses PRFS which are in synchronism with the repetition pulses PRF.

The determination of the focal position and the gate width for the pulse wave measurement is for the first time explained.

When the change-over circuit 41 is changed-over by the control of the control unit 11 and the pulser 42 is connected to the probe 3, the slice pulse generating circuit 43a and the pulser 42 are rendered into an operable condition. In response to the slice pulses PRFS and in synchronism thereto, the synchronous pulses SP are produced which are applied from the slice pulse generating circuit 43a to the pulser 42. In response thereto from a signal transmission terminal 42a of the pulser 42 via the change-over circuit 41, signal transmission pulses TP are applied to the probe 3 with a predetermined period to activate the same. An echo obtained from the sample 17 with respect to a transmission signal wave T (see FIGS. 4(a), 4(b) and 5(b)) generated at the moment is converted into an electrical signal via the probe 3 and the converted electrical signal (echo reception signal) is received by the reception signal amplifying circuit (hereinbelow called receiver) 44 via a reception terminal 44a. The received signal is amplified and wave-detected in the receiver 44 and the resultant signal is sent out to a peak detection circuit 5 and a time measurement circuit 6 respectively. A signal reception circuit portion comprises the flaw detector 4, the peak detection circuit 5 and the time measurement circuit 6.

The peak detection circuit 5 incorporates a gate setting circuit 5b which provides a gate at a predetermined position for the output (the wave-detected echo reception signal) from the receiver 44, detects a peak value in the effective echo portion based on the gate set by the gate setting circuit 5b and outputs the same to an A/D converter circuit 7. A gate position adjusting circuit 5a is an adjusting circuit which manually adjusts the gate position set by the gate setting circuit 5b to delay the already set gate position for the burst wave measurement which will be explained later.

The gate position is set depending on the set signal received from the control unit 11 via the interface 8. The peak detection circuit 5 begins time counting, for example, from a count start signal ST (see FIGS. 4(a) and 4(b)) or a detection signal of a surface echo S (see FIGS. 4(a) and 4(b)) in accordance with the set signal to thereby set the gate at a designated position. The count start signal ST is sent out from the control unit 11.

The time measurement circuit 6 is a circuit which measures the lapse time after the pulse wave transmission or after the surface echo detection, determines the lapse time from the detection of the surface echo S or from the count start signal ST to the detection of a peak, and sends out the same to the control unit 11 via the interface 8.

The A/D converter circuit 7 converts an analog signal of the peak value obtained in accordance with the control signal from the control unit 11 into a digital value at 8-bit 256 stages, for instance. The digital value is sent to a bus 14 as input data made processable by a microprocessor (MPU) 9.

With the arrangement described above, the ultrasonic inspection and imaging instrument 20 operates in a normal measurement condition in such a way that the probe 3, for instance, moves by one pitch in the Y-direction after scanning one line in the X-direction to effect scanning in the direction opposite to the X-direction, i.e., the probe 3 scans the sample 17 in two dimensions on the XY plane by effecting so-called reciprocating scanning in the X-direction. The peak value is thus detected in the peak detection circuit 5 at each measurement point allotted at a predetermined pitch, and the MPU 9 fetches the peak value in the form of a digital value. The MPU 9 stores data on these peak values at the measurement points corresponding thereto in a memory 10 in sequence.

In the case of focusing measurement as described later, moreover, scanning in the Z-direction is added in conformity with the scanning of one line in the X- or Y-direction at the time of scanning the XY plane to effect slant scanning; i.e., the scanning slanted in the depth direction (Z-direction). A specific example of the slant scanning will be described later. An invention in which the focusing is performed in the slant scanning is already issued as U.S. Pat. No. 5,179,945 which is also assigned to the present assignee.

When the MPU 9 stores the measured data in the memory 10, the measured data at the respective measurement points obtained in conformity with identification data can be stored by providing the memory 10 with areas in which the identification data at the respective measurement points corresponding thereto are stored.

In addition to the microprocessor 9, a control panel (not shown), the memory 10 for storing various programs and data, an image memory 12, a display 13 and the like are connected to the bus 14. A touch-sensitive screen 15 is fitted to the display 13 and connected via a touch-sensitive screen interface 16 to the bus 14. The touch-sensitive position is read in the MPU 9 through an interruption process. The touch-sensitive screen 15 is used for providing positional information about a graphic display portion on the screen.

The memory 10 is stored with a slant scanning program 10a, a plane scanning program 10b, a focusing program 10c, a wave velocity processing program 10d, a gate processing and setting program 10e, a display processing program and the like. Slant scanning functions Zs=f(x), Zs=f(y) and the like are stored in a parameter storage area 10f in the memory 10.

The slant scanning program 10a is used to set the initial position of the probe unless it is specified. When this program is executed, the MPU 9 computes the Z-coordinate position (height) of the probe 3 to position the probe 3 (see position A in FIG. 3) so that the focal point is located directly on the surface of the sample 17 at the start point of measurement in conformity with the positional relation between the focal length of the probe 3 and the sample 17, the positional relation being input to the MPU 9 beforehand via the control panel (normally the thickness of the sample 17 that the control panel has provided determines the positional relation as the sample 17 is arranged in the bottom of a water tank). Although the probe 3 is positioned in the Z-direction in accordance with its specified setting position, the position previously defined is employed as a reference position (initial position) of the slant scanning unless the setting position is expressly specified.

Simultaneously with the start of measurement, the MPU 9 performs operations, starting with coordinate positions in the Y-direction (or X-direction) of the point of measurement as the point thereof in the Y-direction (or X-direction) is updated according to the slant scanning function Zs=f(y) (or Zs=f(x)) to compute the position Zs of the Z-coordinates. The MPU 9 further controls slant scanning in the Z-direction as well as the scanning in the Y-direction (or X-direction) on the basis of the computed Z-coordinates. The coordinates in the Z-direction on which the probe 3 is positioned are determined by the values computed by the slant scanning functions. Although the details of the slant scanning are explained in the U.S. Pat. No. 5,179,945 referred to above, hereinbelow the slant scanning is briefly explained primarily for an example wherein the scanning in the depth direction is effected in conformity with the subscanning in the Y-direction. This is also the case with the scanning in the depth direction in conformity with the X-direction scanning in which merely the slant scanning function Zs=f(x) is used in place of the slant scanning function Zs=f(y) and there are no substantial differences therebetween. The U.S. Pat. No. 5,179,945 is explained based on the latter example.

When the slant scanning f(y) is a primary function, the probe 3 moves in the Z-direction (height direction) with a predetermined pitch as the coordinates in the Y-direction are updated. Consequently, the probe 3 normally approches the sample 17 with the predetermined pitch as the subscanning in the Y-direction is effected. The sample 17 is thus scanned by the probe 3 on the plane slanted as viewed from its side.

Figures 4A, 4B:
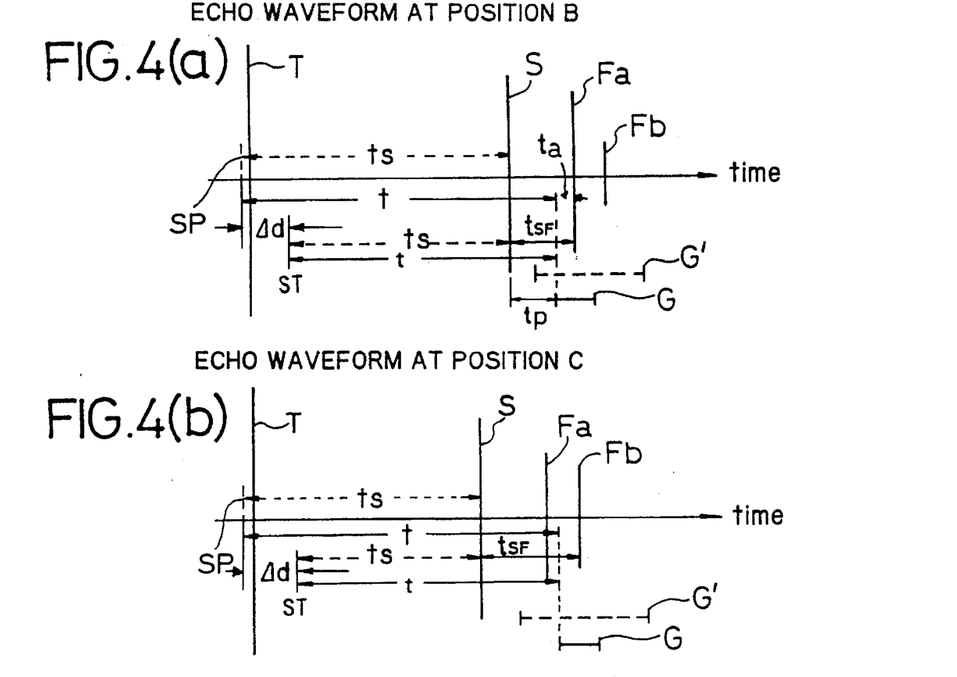
FIGS. 4(a) and 4(b) are explanatory views showing relationships between gate position and gate width which are respectively set for an echo reception signal and for a defect.

The above is explained in detail while taking up an example in which the sample 17 includes two closely lying junction faces 17a and 17b with reference to FIG. 3. When the probe 3 is at the reference position, the focus thereof is on the surface of the sample 17 (position A). When gradually lowering the focus position at first the focus comes on the junction face 17a (position B), subsequently comes on the junction face 17b (position C) and then the focus moves into the interior of the sample 17 (position D). FIG. 4(a) shows a relationship between echo waveform and gate at the position B and FIG. 4(b) shows a relationship between echo waveform and gate at the position C. In these figures, T represents a signal transmission wave, S a surface echo, Fa a reflection echo from the junction face 17a, Fb a reflection echo from the junction face 17b, G and G' represent gates, and these positions are shown along the time axis tm. Further, Sp as appears immediately before the signal transmission wave T and is indicated by a dotted line is a synchronous pulse which is added as a reference and a signal transmission pulse TP mostly overlaps with the signal transmission wave T.

The plane scanning program 10b is an ordinary two-dimensional scanning program. The MPU 9 executes this program, and when the Z-coordinates (height) of the probe 3 are set accordingly, the MPU 9 causes main scanning in the X-direction with a predetermined pitch, and subscanning in the Y-direction with the height (Z-coordinates) fixed.

Incidentally, the measurement pitches in the X- and Y-directions are set at a preset distance in the slant scanning program 10a and the plane scanning program 10b. The measurement pitch in the Y-direction may be the same as, or coarser than, that in the X-direction.

In the case of the focusing program 10c, a measurement point nearest to the position of the Y-coordinate on the picture of the display 13 designated by the touch-sensitive screen 15 is indexed, and the Z-coordinate on the scanning line of the probe 3 is obtained from the slant scanning function f(y). The probe 3 is thus positioned. Further, in case that a so called bit map display is effected on the display 13 in which the pixels of the picture displayed correspond 1:1 to the measurement points, when a certain pixel is designated the corresponding measurement point is immediately indexed.

The wave velocity processing program 10e is a program which calculates a wave velocity in the sample 17 based on the data measured by the slant scanning and the corresponding time measured by the time measurement circuit 6. A specific example thereof is mentioned with reference to FIGS. 3, 4(a) and 4(b). Assuming that the water path difference between when the probe 3 focuses on the surface of the sample 17 and when the probe 3 focuses on the junction face 17a is dz and the focus depth in the interior of the sample 17 from the surface thereof is df, a ratio of wave velocity in the sample/wave velocity in the water, in that Cs/Cu is almost the same as dz/df under the condition that the focal distance of the probe 3 is sufficiently larger than the diameter of the piezoelectric transducer in the form of probe 3. By making use of the above relationship the wave velocity can be calculated. In the above case the focal distance of the probe 3 is assumed to be already known.

In the above relationship, auxiliary conditions therefor are also normally equivalent, therefore a relationship Cs/Cw= dz/df stands. Further, when modifying the above equation by making use of the fact that the lapse time tsf from the point of the surface echo to the junction face 17a is expressed as tsf=2×df/Cs, the wave velocity Cs in the sample 17 is expressed by the following equation including a square rooting operation;

$$Cs=(2\times Cw\times dz/tsf)^{1/2}$$

Further, although the lapse time tsf from the surface echo S to the defect echo Fa (Fb) is measured by making use of the time measurement circuit 6, the lapse times measured for respective echoes during the ultrasonic measurement can be stored separately in the time measurement circuit 6 and thereafter the wave velocity can be calculated by fetching the stored values and by determining the lapse time tsf. Further, after being designated of a position to be measured (an objective echo and the like) the time measurement circuit 6 can perform the lapse time measurement therefor. Still further, the lapse times can be measured as indicated by a dotted line with reference to a count start signal ST which is set at a predetermined position for starting time counting. In this instance the count start signal ST is provided from the control unit 11.

The gate processing and setting program 10e also performs calculation of the width of the gate G and G' and the like (see FIGS. 4(a) and 4(b)). When the wave velocity in the sample 17 is unknown, the gate is set with a broad width (gate G'), but after determining the wave velocity of the sample 17, the gate with a narrow width is set in accordance with the water path, wave velocity and the focal position (gate G). When the wave velocity is determined an accurate refractive index therein can be calculated, therefore the focal position in the interior of the sample 17 is correctly predicted. Thus when the focal position can be correctly predicted a reliable measurement can be performed even with a narrow gate width without missing the focal position.

Then, in response to an input of a value ta from the control panel an optimum gate width G among many narrow gate widths for a burst wave measurement is calculated in relation with the position of the defect wave Fa or the defect wave Fb. Further, if it is necessary to adjust the gate position tp determined by the surface echo S obtained during the pulse wave measurement for the burst wave measurement, an optimum gate position tp is calculated in relation with the selected gate width G.

Based on either the thus calculated gate position tp or the manually adjusted determined gate position tp as explained above, time t, representing the gate position determined with reference to a reference position of the time count for generating a burst wave or with reference to the count start signal ST or the synchronous pulse SP is calculated by making use of the water path and the previously determined wave velocity. Then, a value which is determined by subtracting a pulse wave delay time $\Delta t$ from the above calculated time t, i.e. tb=t−$\Delta t$, is stored in a predetermined area in the parameter storage region 10f as a gate position tb for use during the burst wave measurement.

The time t can be provided simply as a sum of times ts from the leading edge of the synchronous pulse SP to the surface echo S, and the gate position tp determined from the surface echo S; however as shown in the figure the time t can be determined with reference to the above count start signal ST.

After obtaining the lapse time tsf, the gate processing and setting program 10e calculates a gate position time tp from the surface echo S based on the obtained lapse time and sets the gate in a range covering the defect wave Fa. The time tp can be calculated automatically according to the equation of tp=tsf−ta, wherein ta is a preset value, or alternatively after manually adjusting the time value ta from the control panel (not shown) the gate position time tp can be calculated according to the above equation.

Figure 5A:
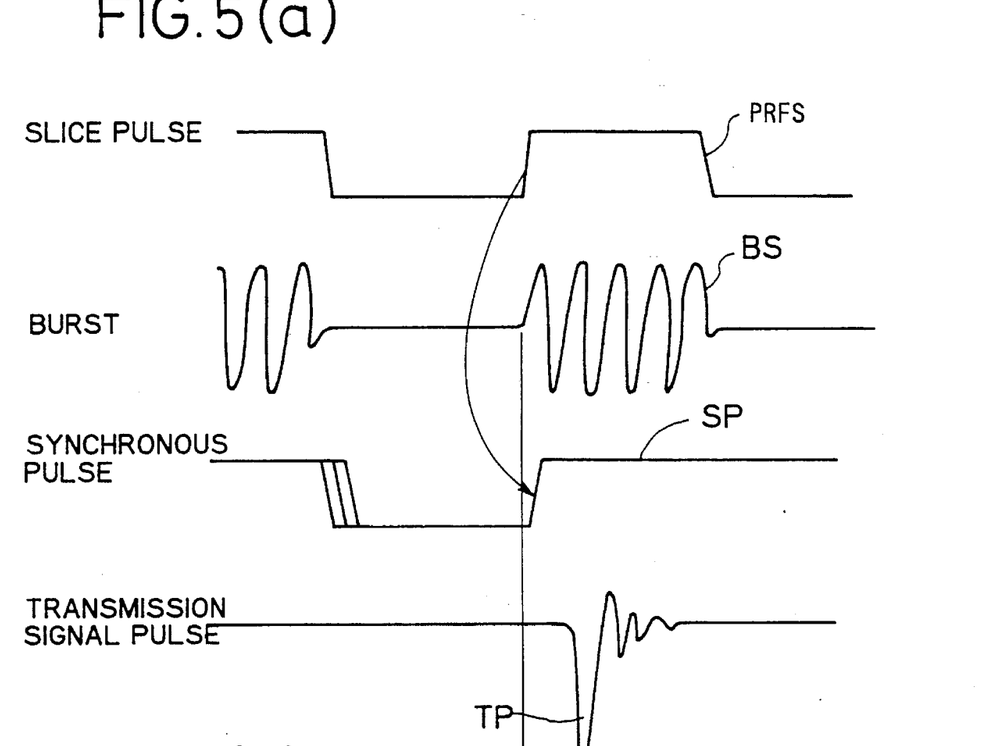
FIG. 5(a) is an explanatory view showing a relationship between a pulse signal generation in synchronism with a slice pulse of a burst signal.
Figure 5B:
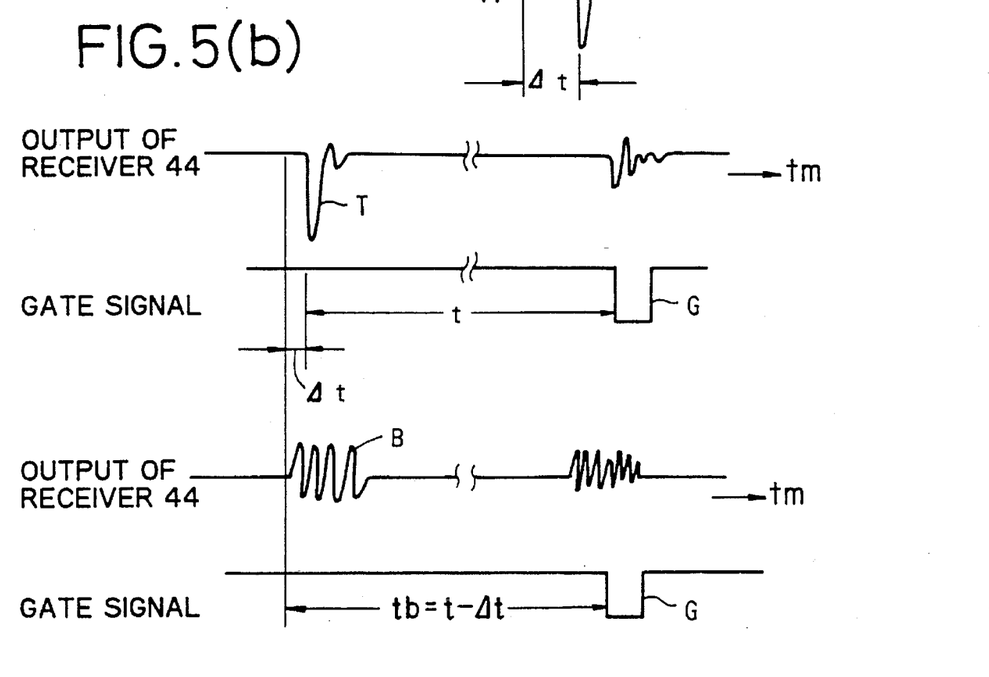
FIG. 5(b) is an explanatory view showing a difference of gate positions for a pulse wave measurement and for a burst wave measurement.

The gate processing and setting program 10e further calculates the above indicated gate position tb for the burst wave measurement, in that, based on the gate position tp at the selected height of the probe 3 a gate position t from the synchronous signal SP or the count start signal ST is calculated, and using the calculated gate position t, tb=t−$\Delta t$ (see FIG. 5(b)) is calculated and stored in the predetermined area in the parameter storage region 10f as the gate position for the burst wave measurement as indicated above.

A relationship between the pulse wave measurement and the burst wave measurement is now explained. Assuming that a burst signal BS (burst wave), for example a burst signal BS of 100 MHz, is sliced out by slice pulses PRFS, as shown in FIG. 5(a), synchronous pulses SP produced in synchronism with the leading edge of the slice pulses PRFS are applied to the pulser 42 to activate the same and causes to generate the signal transmission pulse TP.

The deviation quantity between the leading-up timing of the signal transmission timing TP and the leading-up timing of the burst signal BS as shown in FIG. 5(a) corresponds to the previously explained delay time $\Delta t$.

Since the delay time $\Delta t$ is the deviation quantity between the leading-up timing of the signal transmission timing TP and the leading-up timing of the burst signal BS, the delay time $\Delta t$ can be measured. For example, the delay time $\Delta t$ can be obtained by observing via an oscilloscope the outputs from the pulser 42 and the burst wave generator 43 at the terminal position of the probe 3. The obtained value is stored beforehand in the parameter storage region 10f.

Since the transmission paths of the burst signal BS and the signal transmission pulse TP to the probe 3 are the same, if a deviation quantity due to the difference in methods between the pulse wave measurement and the burst wave measurement is neglected, a deviation quantity between the gate position obtained by the pulse wave measurement and the gate position G necessary for the burst wave measurement is −$\Delta t$ as shown in FIG. 5(a), in that the gate position for the burst wave measurement comes before the gate position for the pulse wave measurement by $\Delta t$.

Further, the gate position (time value t) for the pulse wave measurement can be measured from the pulse wave generation. However, normally the counting thereof is started with reference to the count start signal ST which is delayed by a predetermined time $\Delta d$ with reference to the synchronous signal SP. On the other hand, the gate position (time value tb) for the burst wave measurement uses the leading edge of the slice pulse PRFS as the reference. In this instance since the time value of the gate position is shortened by $\Delta d−\Delta t$, the gate position for the burst wave measurement is delayed by $\Delta d−\Delta t$. Accordingly, whether the gate position for the burst wave measurement is to be delayed or advanced is determined depending on the setting relation of the gate positions for the pulse wave measurement and the burst wave measurement. Some quantity of deviation caused by the setting is adjusted by the gate position adjustment circuit 5a (see FIG. 1) which is designed to adjust the deviation quantity due to the difference in methods between the pulse wave measurement and the burst wave measurement.

Further, in addition to the above Δt, there the gate position must be further delayed by a predetermined time td because the timing of the activation pulse for the pulse wave measurement is predetermined through the activation of the pulser 42. In this instance, the gate position set for the burst wave measurement is represented by t−(Δt+td) in place of the above indicated t−Δt. Further, when Δt<<td, the gate position is represented by t−td.

The gate position t is, for example, about several tens μsec from a reference position and the gate position adjustment is on the order of a few μsec. Contrary thereto, the gate width is on the order of a few tens ns to a few nsec. Further, although in the above example using the burst wave (burst signal BS) having a frequency of 100 MHz the relationship between the pulse wave and the leading timing of the burst wave is explained, the frequency from about 10 MHz to 200MHz can be used for the burst wave and the number of waves in the burst wave (burst signal BS) measurement is from a few cycles to ten and a few cycles. Accordingly, when the frequency used in the burst wave measurement is varied, the peak position deviates at most by about a half cycle with respect to the gate position for the pulse wave measurement; however, the deviation quantity can be adjusted by the gate position adjustment circuit 5a.

The picture obtained from the slant scanning is a planar picture (called a slant picture herein) resulting from transmission in the depth direction in which the focusing position of the probe 3 gradually becomes deeper in association with subscanning in the Y-direction. The respective pixel positions (positions corresponding to the Y-coordinates) of the picture and the distance between the sample 17 and the probe 3 represented by the Z-axis coordinate position (Z-coordinate values on the scanning line) of the scanning mechanism are correlated by the slant function f(y). Namely, the above mentioned Z-coordinate values on the scanning line can be determined by obtaining the measurement points (Y-coordinates) in the Y-direction from the positions of display data designated on the screen. The calculation of the Z-coordinates need not always rely on the slant function f(x) but may be performed by storing the position (height) of the Z-coordinate of the probe 3 in the memory 10 as measurement at each measurement point proceeds to make the measurement point and the height of the probe 3 correspond to each other. When the picture on the display 13 is displayed in a form of a bit map, the data on the height of the probe 3 may be stored in the memory 10 in conformity with the displayed data.

Figure 2:
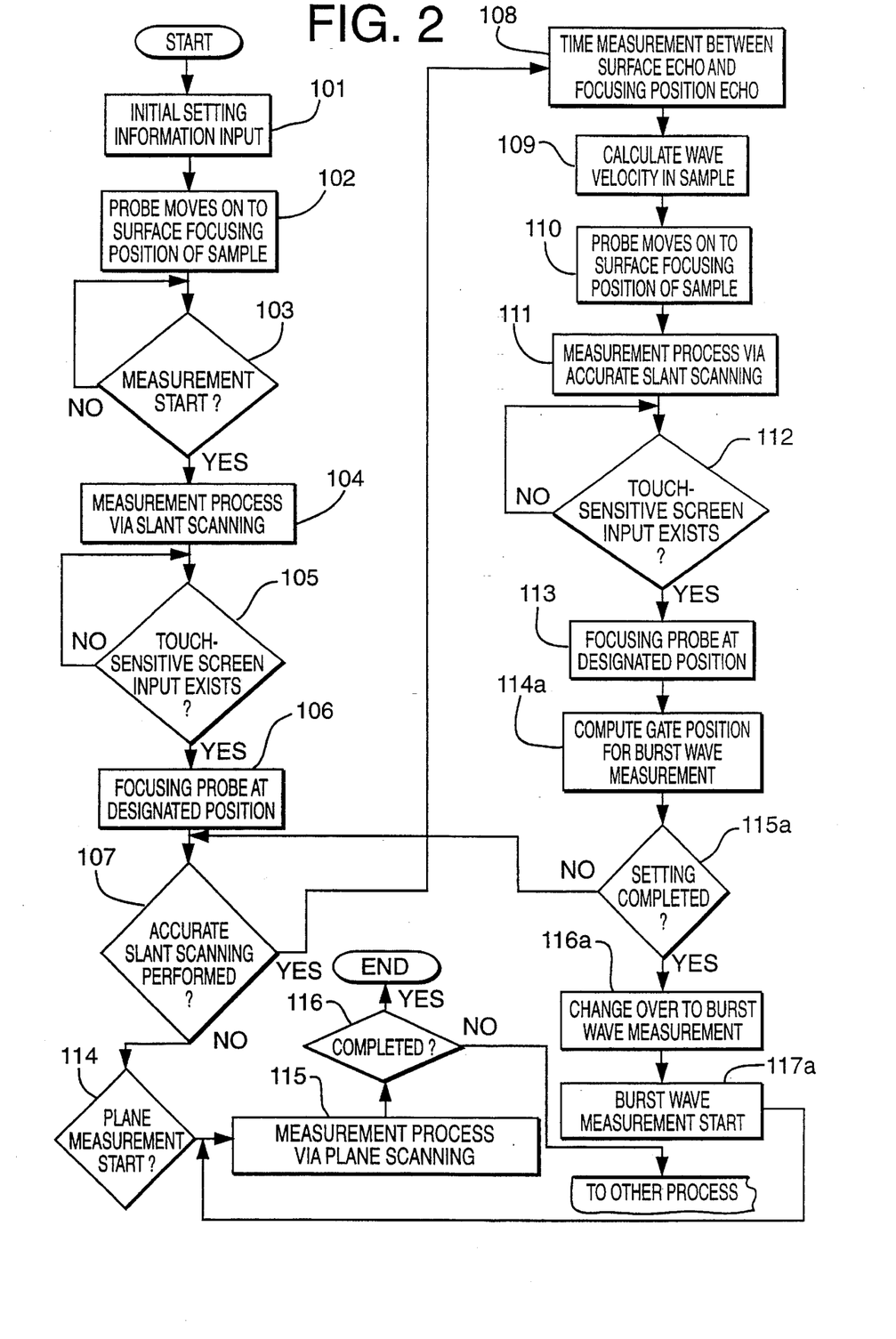
FIG. 2 is a flowchart showing processes of focusing and the like and a burst wave measurement process.

Subsequently, the setting of the height of the probe 3 with respect to the sample 17 and of the gate width and the burst wave measurement with the control unit 11 are explained according to the flowchart as shown in FIG. 2.

The processing of FIG. 2 is started when a predetermined function key is pressed and initial data including the focal length of the probe 3 and the thickness of the sample 17 are keyed in at the control panel at step 101. On the other hand, the set values most frequently used in the ultrasonic inspection and imaging instrument such as the generation period of the signal transmission pulses TP of the ultrasonic flaw detector 4, and the gate width G' of the peak detection circuit 5 and the like, are prestored in a predetermined area of the memory 10.

In this case, the MPU 9 sets necessary data in various circuits via the interface 8 by reference to the set values stated above. The gate width of the peak detection circuit 5 is then set in a range of about 0.1 μs to several μs, for instance. Although these set values are variable, there will be no problem posed functionally in case they are left unchanged. In other words, setting alteration of the broad gate width G' is unnecessary unless use can be made of knowledge about ultrasonic measurement.

At step 102, the probe 3 is situated at a measurement start position (initial position). Namely, the distance between the sample 17 and the probe 3 is set so that the focal point of the probe 3 as a reference position of the probe 3 in its height direction is located right under the surface thereof (see position A in FIG. 3).

At step 103, a loop waiting for a measurement start key on the control panel to be pressed is entered to see if the start of scanning is keyed in.

When the information thereabout is keyed in, slant scanning measurement is started at step 104 and the MPU 9 executes the slant scanning program 10a, whereby updating of the measurement point (measurement position) in the Y-direction as well as slant scanning the Z-direction on the sample 17 are effected. As a result, the probe 3 is moved by one pitch in the Y-direction, and the distance between the sample 17 and the probe 3 is gradually narrowed.

The multicontrast data on the peak value obtained in conformity with each measurement point as the XY slant scanning in the Y-direction proceeds are stored as display data at the address of the image memory 12 corresponding to XY-coordinates in accordance with the XY-coordinates of the present scanning position. The display data stored in the image memory 12 are subsequently transferred to a video memory of the display 13 and its picture is displayed under the control of a controller contained in the display 13. The picture displayed at this time constitutes a detected flaw image resulting from the slant scanning in the depth direction.

Since the detected flaw image is a measurement picture under the gate G' of a broad width, when the two junction faces 17a and 17b in the interior of the sample 17 lie close to each other, the reflection echoes Fa and Fb coming from the junction faces simultaneously enter into the gate making discrimination thereof impossible. Therefore, in the measurement picture the position B showing an intense echo (see the junction face 17a in FIG. 3) is displayed comparatively clearly; however the important target position C (see the junction face 17c in FIG. 3) becomes blurred, being affected by the junction face 17b.

At step 105, the focusing program 10c is initiated and an operator performs a focusing operation by designating a clear display position on the screen. Naturally, it is desired to designate the target position C; however, since the position C is blurred, for the time being as an alternative thereof when the operator touches the touch-sensitive screen 15 at another clear display position, for example the position corresponding to position B, the process moves to step 106.

Thus an interruption signal caused by the touching operation is input to the MPU 9 via the interface 16. As a result, the MPU 9 performs the focusing operation at the step 106.

Namely, when the MPU 9 receives the interruption signal, the MPU 9 indexes the display coordinate of the position B displayed on the display 13 based on a position signal from the touch-sensitive screen 15, extracts the Y-coordinate thereof and computes the Z-coordinate on the scanning line from the measurement point thus extracted according to the slant function f(y) so as to place the probe 3 at the computed position. The computed position is stored at a predetermined position in the parameter storage region 10f of the memory 10. The computed position represents the height at which the focus of the probe 3 comes on the junction surface 17a corresponding to the position B.

At step 107, the process enters into a loop waiting for a key input on the control panel and it is determined whether the slant scanning measurement is again performed based on the input key state. When measuring the junction face 17a the focusing operation is already completed, and no duplicate slant scanning operation is needed. Therefore, in this instance the process moves to step 114. In the present example, a measurement on the junction face 17b is required, so the process moves to step 108 to perform again a slant scanning measurement. Further, if the image obtained by the first slant scanning is not so clear and it is presumed that the position of the junction face 17a is not correct, a slant scanning measurement is again performed on the junction face 17a.

At step 108, the wave velocity processing program 10d is initiated. Then at first, with regard to the junction face 17a on which the focusing is presently made, the lapse time from the surface echo S to the concerned junction face 17a is measured. Subsequently, at step 109 the MPU 9 executes the wave velocity processing program 10d and the wave velocity Cs in the sample 17 is computed according to the method as explained above. Further, based on the clarification of the wave velocity Cs the gate processing and setting program 10e causes to store a proper narrow width value of gate G (see FIG. 4(a)) for the subsequent burst wave measurement as the gate width used for the subsequent measurement in a predetermined position in the parameter storage region 10f of the memory 10. In this instance, as opposed to the automatic setting, the gate width can be input and set through the control panel (not shown) so as to be suitable for the burst wave measurement. Of course, the set gate width is stored in a predetermined position in the parameter storage region 10f as data used for the measurement. Even when the gate width is determined narrow in this measurement, the focusing position is accurately estimated because the refraction factor and the like are clarified owing to the determination of the wave velocity. Accordingly, even with a narrow gate width the gate position can be reliably correlated to the focusing position. Further, because of the narrow gate width the defect echoes Fa and Fb can be clearly separated (see G in FIGS. 4(a) and 4(b)).

Further, in this instance the gate position for the pulse wave measurement is set in accordance with the focusing position of the probe 3, and the time tp after detecting the surface echo is computed and is set by the control unit 11 at the peak detection circuit 5. When performing the slant scanning in the Y-direction, the gate time to be set is determined in the following manner, in that after obtaining respective Z-coordinate measurement positions (probe heights) which are determined in response to the scanning distance in the Y-direction and in accordance with the slant function, the focusing position of the probe 3 in the sample 17 in the depth direction is indexed based on the obtained measurement position, and then the time for the gate setting is computed with reference to the surface echo S with regard to the concerned focusing position. The gate processing and setting program 10e performs the above explained processing operations. The computed result tp is provided for the slant scanning to the peak detection circuit 5 via the interface 8 from the MPU 9 as well as stored in a predetermined area in the parameter storage region 10f of the memory 10 as the proper gate position tp from the surface echo S.

At steps 110 and 111, the processes at steps 102 and 104 are repeated, in that the slant scanning measurement is again performed and the detected flaw image of the slanted face is again displayed. In this instance, since the same program is used, remeasurement on the same range as the previous one is performed. However, the remeasurement and the redisplay can be performed on the process parts after the focusing is made on the position B at step 106. In this instance, the program is required to perform the processes in response to the data designating a range inputted via the control panel, and therefore the processes become somewhat complicated. However, the process time as a whole is shortened and the work efficiency is improved. Further, at this stage the probe height previously designated via the control panel is stored as a first focusing position in the memory 10.

The detected flaw image thus measured and displayed under the gate G of the narrow width shows an improved imaging resolution, and thus the respective images of closely lying junction faces 17a and 17b are clearly displayed. Namely, not only the position B corresponding to the junction face 17a but also the position C corresponding to the junction face 17b are clearly displayed.

After noting the clear images of the positions B and C, the operator designates at steps 112 and 113 the clear display position C on the picture via the touch-sensitive screen 15 in the same way as at step 105. Thereby, the focusing position for the display position C is stored in the memory 10. In this instance, if it is required to perform a measurement on the first designated display position B, such is simply performed by touching the display position B again.

At the subsequent step 114a, the MPU 9 executes the gate processing and setting program 10e wherein the probe 3 is positioned at the previously determined probe position, the time value tsf from the surface echo S to following defect echo Fb as shown in FIG. 4(b) is obtained from the time measurement circuit 6, the gate position t from either the synchronous signal SP or the count start signal ST is computed based on the time value tsf, and the gate position for the burst wave measurement tb=t−Δt is computed and is stored in the parameter storage region 10f of the memory 10.

Then, at step 115a it is judged whether or not the setting operation is completed. When it is judged that the setting operation is completed, the YES condition stands and the process moves into step 116a to enter into the burst wave measurement. If judged not completed, the NO condition stands and the process returns to step 107.

At step 116a, the MPU 9 moves into the burst wave measurement mode, and at first a control signal is sent out to the change-over circuit 41, the change-over from the pulse wave measurement mode to the burst wave measurement mode is performed and the burst wave generator 42 is selected. Thereafter, at step 117a the burst wave measurement is started. In this instance, the probe height and the gate width are already determined at values suitable for the burst wave measurement during the pulse wave measurement. After the value tb(=t−Δt) stored at the parameter storage region 10f is read out as the gate position, the respective parameters are then set. Further, the set gate position is manually adjusted to an optimum position for the burst wave measurement via the gate position adjustment circuit 5a, and the set gate width is somehow adjusted to an optimum gate width for the burst wave measurement. When the gate position tb(=t−Δt) uses the count start signal ST as the reference, an adjustment (tb=t+Δd−Δt) for the deviation quantity Δd with respect to the leading-up timing of the slice pulse PRFs is performed and then the gate position is set.

FIGS. 6(a) and 6(b) show relationships between the gate positions and gate widths in the pulse wave measurement and for the burst wave measurement in the above explained instance. FIG. 6(a) shows a relationship between the gate position and the receiving echo signals in the pulse wave measurement and FIG. 6(b) shows a relationship between the gate position and receiving echo signals in the burst wave measurement. The gate position for the burst wave measurement is placed at t−Δt+δ, wherein δ is a value manually adjusted via the gate position adjustment circuit 5a. The gate position represents the position at which the deviation quantity caused between the pulse wave measurement and the burst wave measurement is corrected, and is placed at the echo position from the interface in the sample. As a result, the peak values caused by the interference waves of the burst waves are successively sampled out as the measurement values in response to the planar scanning via the control unit 11.

The detected flaw image thus obtained through the burst wave measurement under the narrow gate width shows a high imaging resolution. Further, when setting the gate with a narrow gate width, the gate position adjustment circuit 5a, which corrects the deviation in the positions for the pulse wave measurement and for the burst wave measurement, functions particularly advantageously.

Alternatively, during the burst wave measurement, a gate can be set having a width which can cover all of the interference waves including the defect echos and the surface echo and can neglect the above indicated deviation quantity Δt. In this instance, because of the provision of the gate position adjustment circuit 5a, the correction by the gate position adjustment circuit 5a of the deviation in the gate positions for the pulse wave measurement and for the burst wave measurement is performed in such a manner that the deviation is set at Δt=0 and the gate position t during the pulse wave measurement is used as the gate position tb=t for the burst wave measurement.

When the burst wave measurement is performed successively after completing the pulse wave measurement as in the above explained embodiment, the probe height (that the distance between the sample and the probe) is not necessarily stored in the memory. Instead, while fixing the position of the probe determined during the pulse wave measurement, it is enough if the gate position and the gate width stored in the memory are only read out.

Further, in the present embodiment the focusing is performed through the touch-sensitive screen for the image obtained by the slant scanning. However, without relying on the slant scanning a focusing position obtained by a manual adjustment can be simply inputted through the control panel or the keyboard. Similarly, the values with regard to the gate position and the gate width obtained through manual adjustment for the pulse wave measurement can be respectively inputted and thereafter the gate position and the gate width optimum for the burst wave measurement can be computed and set.

In the present embodiment, the pulse wave measurement and the burst wave measurement are associated, in that the burst wave measurement is designed to automatically start after completion of the pulse wave measurement. However, these measurements can be designed to be operated independently and to be selected depending on necessity.

Further, the peak is not necessarily essential, though the peak value of an echo is detected in the embodiment shown. In this case, it may be arranged to detect an echo level, including the stress of an echo.

We claim:

1. An ultrasonic inspection and imaging instrument in which an ultrasonic probe is activated via burst signals, an ultrasonic measurement is performed at a predetermined inspection portion in the interior of a sample with burst waves and a result of the ultrasonic measurement is displayed in a form of image, said instrument comprising:

a pulse generator;

a burst signal generator which generates the burst signals;

a focusing type ultrasonic probe which covers a frequency of output pulses of said pulse generator and a frequency of the burst signals within an oscillation band thereof;

a signal reception circuit portion which receives reception signals from said ultrasonic probe and outputs a signal which has a measurement value; and a control unit having gate position setting means and ultrasonic measurement means;

wherein said gate position setting means activates said ultrasonic probe through the output pulses produced by activating said pulse generator to obtain a first gate position with regard to the inspection portion dependent upon receipt of the measurement value obtained from said signal reception circuit portion, corrects the first gate position to obtain a second gate position for burst wave measurement and sets a gate at the second gate position; and wherein said ultrasonic measurement means activates said ultrasonic probe by the burst signals with the gate at the second gate position having a predetermined gate width and performs said ultrasonic measurement on the inspection portion and displays said ultrasonic measurement result on a display.

2. An ultrasonic inspection and imaging instrument according to claim 1, wherein said burst wave generator generates the burst signals by slicing out a continuous signal by slice pulses, said pulse generator is activated by the slice pulses in synchronism therewith and generates the output pulses and said gate position setting means includes an adjusting means for adjusting a gate position, and obtains the second gate position by correcting the first gate position through adjustment thereof via said adjusting means.

3. An ultrasonic inspection and imaging instrument according to claim 2, wherein said gate position setting means obtains a certain gate position by correcting the first gate position by a deviation quantity between a generation timing of a burst signal and a generation timing of an output pulse, and obtains the second gate position by correcting the certain gate position through adjustment thereof via said adjusting means.

4. An ultrasonic inspection and imaging instrument according to claim 1, further comprising a processor, a memory which stores a first and a second processing program and a gate setting circuit which is provided in said signal reception circuit portion, wherein said gate position setting means is realized by executing the first processing program via said processor and controls said gate setting circuit, the correction of the first gate position is performed via said gate setting circuit and said ultrasonic measurement means is realized by executing the second processing program via said processor.

5. An ultrasonic inspection and imaging instrument according to claim 1, wherein said gate position setting means obtains the first gate position with regard to the inspection portion in response to the measurement value obtained from said signal reception circuit portion and obtains the distance between said ultrasonic probe and the sample and the predetermined gate width for the burst wave measurement with regard to the inspection portion, and wherein said ultrasonic measurement means sets a certain gate width at the second gate position based on the predetermined gate width and performs the ultrasonic measurement with said ultrasonic probe set at the above obtained distance.

6. An ultrasonic inspection and imaging instrument according to claim 5, wherein the distance represents a height of said ultrasonic probe for a slant scanning corresponding to a selected image position in a measurement image obtained by the slant scanning in a depth direction in said sample, and the certain gate width at the second gate position is adjusted with reference to the predetermined gate width.

7. An ultrasonic inspection and imaging instrument according to claim 6, wherein said signal reception circuit portion includes a receiver which amplifies and wave-detects the reception signals, a gate setting circuit which sets a gate for the output signals of said receiver, a peak detection circuit which detects a peak in the output signals obtained from said gate setting circuit, and an A/D converter circuit which A/D converts the output of said peak detection circuit and outputs digitized signals to said control unit, and said gate position setting means includes an adjusting circuit which adjusts the gate position set by said gate setting circuit for correcting the first gate position.

8. An ultrasonic inspection and imaging instrument according to claim 7, wherein said display has a touch-sensitive screen and said selected image position is a certain position detected via the touch-sensitive screen in a measurement image displayed on said display in response to the measurement value obtained by the slant scanning.

9. An ultrasonic inspection and imaging instrument according to claim 8, wherein a selected position in the measurement image displayed on the display in response to the measurement value obtained by the slant scanning under a first gate width having a broad width is detected via said touch-sensitive screen, said ultrasonic probe is positioned at a height corresponding to the selected position, a second gate width narrower than that of the first gate width is selected, the slant scanning is again performed under the second gate width and said selected position is detected via said touch-sensitive screen in the slant scanning under the second gate width, and the gate width at the second gate position is determined based on the second gate width.

* * * * *